June 9, 1959 C. SKIMINA Plant Pat. 1,842
LANTANA PLANT
Filed July 14, 1958
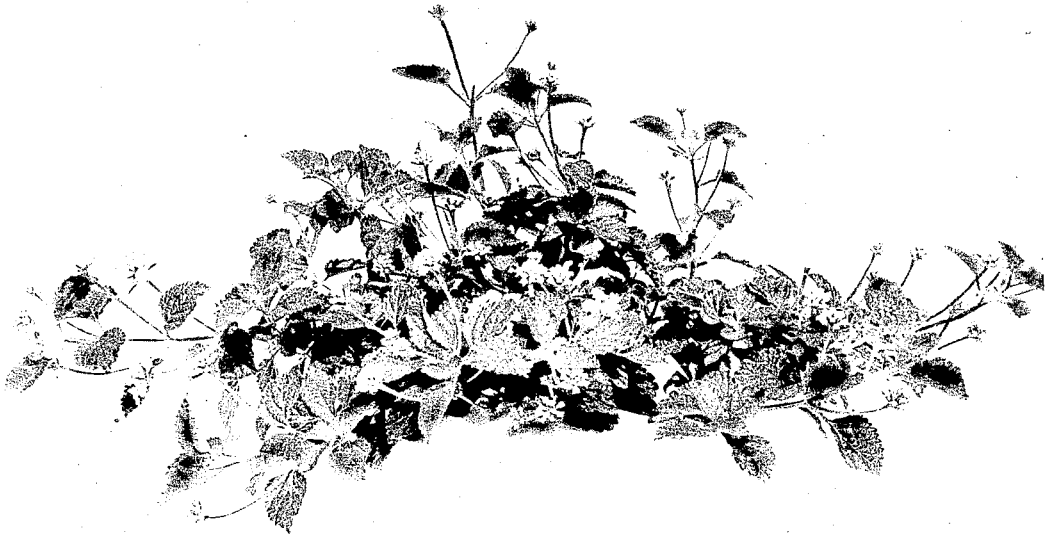
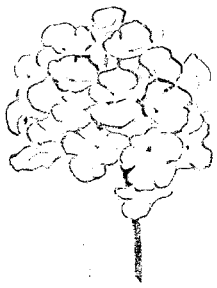
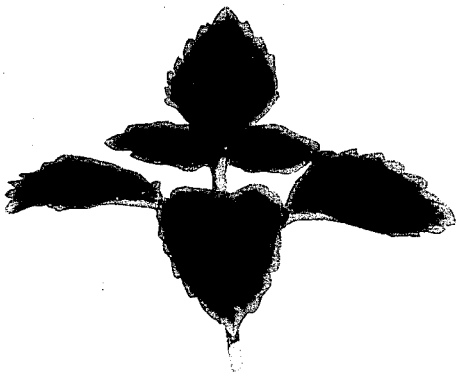
INVENTOR.
CONRAD SKIMINA
BY J. F. Cuneo
ATTORNEY United States Patent Office Plant Pat. 1,842
Patented June 9, 1959

1,842

LANTANA PLANT

Conrad Skimina, Azusa, Calif., assignor to Monrovia Nursery Co., Azusa, Calif., a corporation of California Application July 14, 1958, Serial No. 748,551

1 Claim. (Cl. 47—60)

The present invention relates to a new and distinct variety of plant of the Lantana genus characterized as to novelty by its prostrate growing habit, abundance of large leaves and yellow flowers. This plant has resulted from the cross breeding by me of *Lantana callowiana* Gold Rush, United States Plant Patent No. 1,211, and *Lantana camara* Christine, an unpatented variety, after conducting a considerable number of experiments in southern California, particularly in Los Angeles County.

Cross breeding of the above named species of Lantana has produced a new type as well as a new variety of Lantana that combines some of the characteristic features of each of its parent plants. The new variety of Lantana distinguishes from its parent plant *Lantana callowiana* Gold Rush in that the flowers are a lighter and brighter yellow in color having none of the orange tint of the parent plant flowers, the leaves are considerably larger and are darker in color, and the new plant is a much more vigorous grower. The novel variety differs from *Lantana camara* Christine in that the color of the flowers are Indian Yellow, its growth is prostrate instead of upright and the plant has many branches.

The bloom of the new variety is made up of a group of individual florets arranged in an umbel. The number of florets in the various umbels varies slightly.

The accompanying illustrations include a black and white photograph of my new variety of Lantana that clearly shows its prostrate or trailing habit. The illustrations also include a full color reproduction of a single umbel and a full color representation of a typical leaf branch that shows the size and shape of the leaves as well as their color.

The new variety of Lantana has been reproduced asexually by me in southern California by means of cuttings, and the distinguishing characteristics have been observed to be well established in the resulting plants. It has further been found that the new variety of Lantana cannot be reproduced by sexual means, it does not reproduce true from seed.

A detailed description of the novel variety of Lantana follows. All references to color names and numbers which appear in the description are based on the Horticultural Colour Chart adopted by the British Colour Council.

*The plant*

Nature and growth: The plant is best described as being of the trailing or prostrate type that puts forth many branches as is readily seen in the accompanying black and white photograph. The plant forms a densely foliated shrub having vinelike stems that vary from two and a half to three feet in length. The growth emanates from a central root structure.

Stems: The stems are slender and vinelike. New stems are succulent at first but as they become older they are better described as woody; when they have attained maturity they become stiff and brittle.

Leaves: The foliage of the plant is persistent and is moderately dense having the following characteristics:

*Size.*—The leaves will average about one inch in width and are usually about one and one quarter inches in length.

*Shape.*—The leaves are broadly ovate, having serrated edges, the apex of the leaf being acute. The base of each leaf is usually rounded.

*Arrangement.*—The arrangement of the leaves is opposite. Each leaf is attached to its respective stem by a short peduncle.

*Color.*—The predominant leaf color is Spinach Green 0960.

*Appearance and texture.*—The leaves are slightly creased and exhibit a leathery appearance. The surfaces of the leaves are sparsely pubescent. The ribs are quite prominent on the under side of the leaf.

*Aroma.*—The leaves have an aroma that resembles somewhat the aroma of oil of eucalyptus and is also reminiscent of the odor of sage.

Blooming habit: The plant is a profuse bloomer.

*The flower*

Arrangement: The individual flowers are grouped together in the form of a substantially hemispherical umbel that varies in size from one to one and a quarter inches in diameter. Each umbel contains from 19 to 23 individual florets. The umbels are formed on strong axillary peduncles that average from two and three quarter to three inches in length. The peduncles that support the flower umbel show no pubescence. The flowers are found almost exclusively on terminal growth.

Florets:

*Size.*—The individual florets are quite small varying between five sixteenths and three eighths of an inch in width.

*Color.*—The color of the florets is Indian Yellow 6/1.

*Aroma.*—The florets have a very faint aroma that resembles that of the leaves.

Having described my invention, I claim:

The new and distinct variety of Lantana plant, substantially as herein shown and described, characterized especially by its abundance of faintly aromatic yellow flowers and its combination of the prostrate, trailing growth habit of *Lantana callowiana* Gold Rush, with the larger and darker leaves of *Lantana camara* Christine.

No references cited.